United States Patent [19]

Brown

[11] Patent Number: 4,834,080
[45] Date of Patent: May 30, 1989

[54] DRILL BIT GUIDE

[76] Inventor: Byron L. Brown, 2315 Hendricks, Fort Smith, Ark. 72903

[21] Appl. No.: 77,177

[22] Filed: Sep. 11, 1987

[51] Int. Cl.$^4$ .............................................. A61F 5/04
[52] U.S. Cl. ......................... 128/92 VP; 128/92 VD; 623/16
[58] Field of Search .......... 128/92 VD, 92 V, 92 VY, 128/92 VV, 92 VW, 92 R, 92 Z, 92 ZZ, 92 ZW; 623/23, 22, 16, 20

[56] References Cited

U.S. PATENT DOCUMENTS

| 3,814,089 | 6/1974 | Deyerle | 128/92 VD |
|---|---|---|---|
| 4,185,624 | 1/1980 | Gentile | 128/92 Z |
| 4,299,212 | 11/1981 | Goudfrooy | 128/92 ZW |
| 4,349,017 | 9/1982 | Sayegh | 128/92 Z |
| 4,357,716 | 11/1982 | Brown | 623/23 |
| 4,404,692 | 9/1983 | Eftekhar | 623/22 |
| 4,646,729 | 3/1987 | Kenna et al. | 128/92 VD X |
| 4,678,471 | 7/1987 | Noble et al. | 128/92 VD X |
| 4,718,909 | 1/1988 | Brown | 623/16 |

Primary Examiner—Mickey Yu
Assistant Examiner—Kevin G. Rooney
Attorney, Agent, or Firm—Sigalos, Levine & Montgomery

[57] ABSTRACT

An improved drill bit guide which enables a prosthesis fixture to be attached to the femoral cortex of a resected femur with the use of drill bits or fixation pins passing through the fixture and through the femoral cortex more quickly and accurately than has been possible previously.

21 Claims, 3 Drawing Sheets

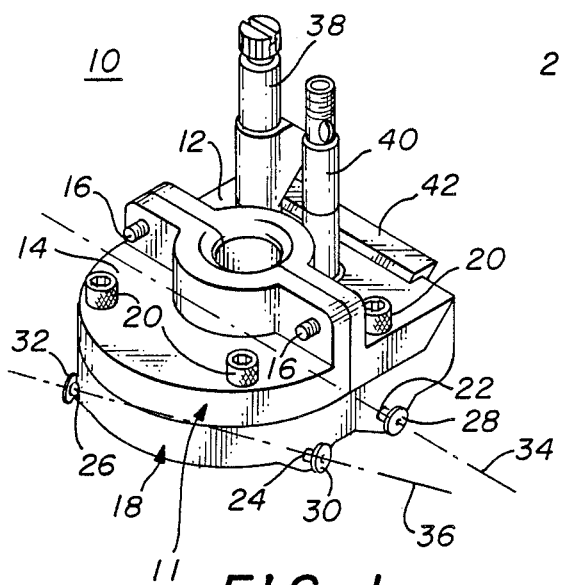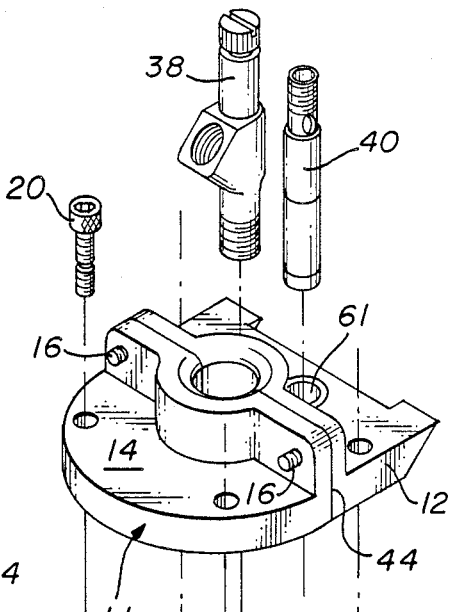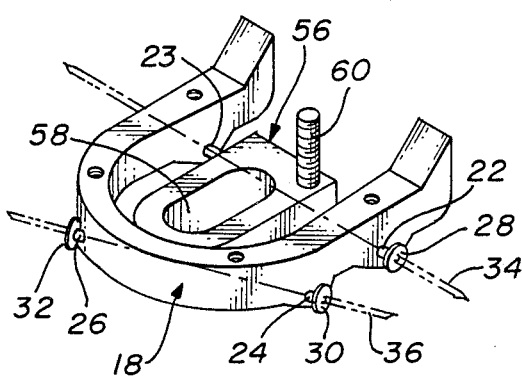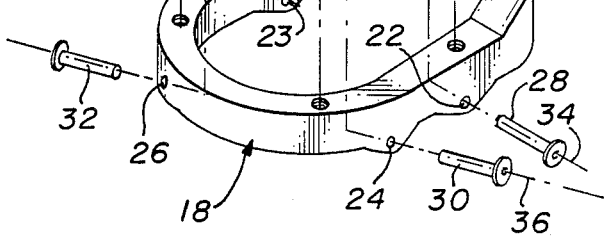
FIG. 1
FIG. 2
FIG. 3

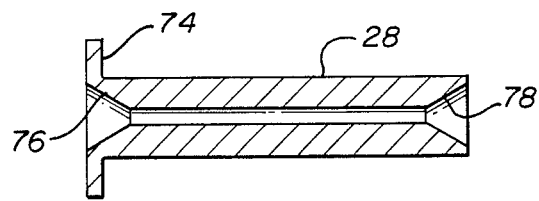
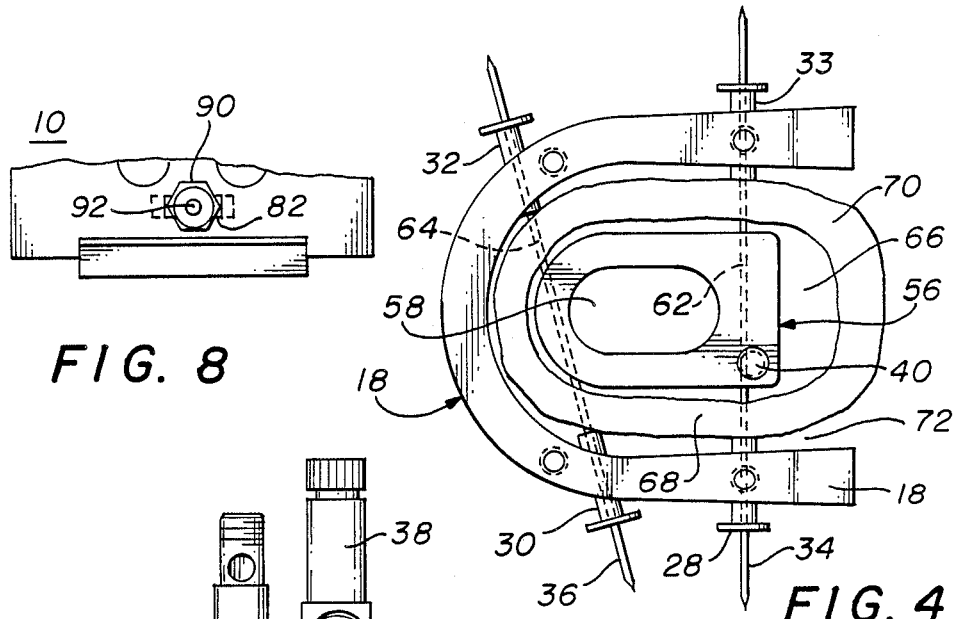
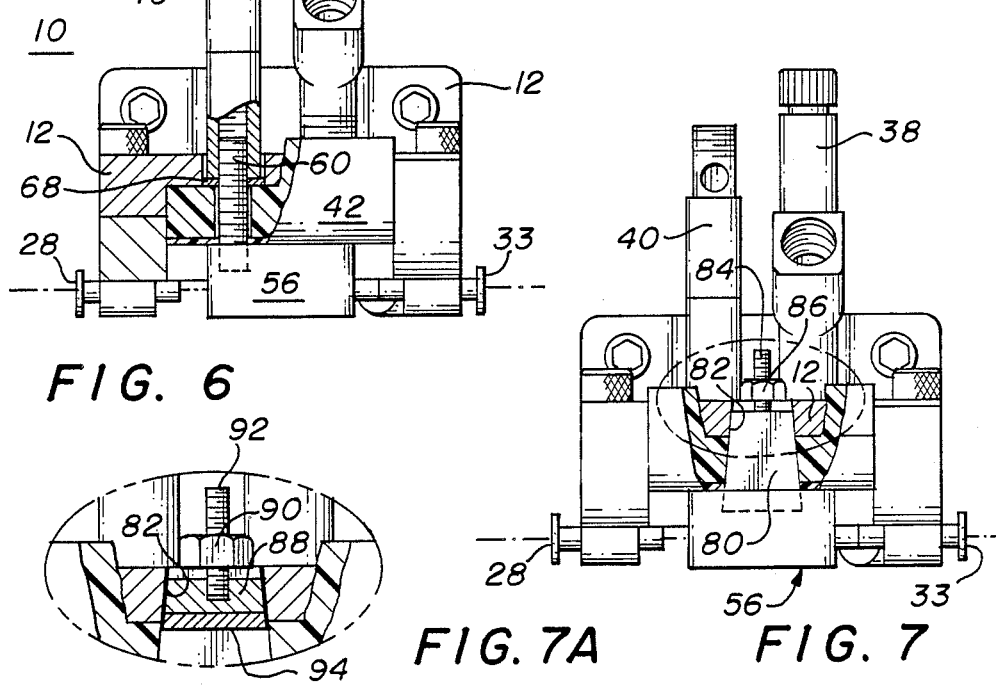
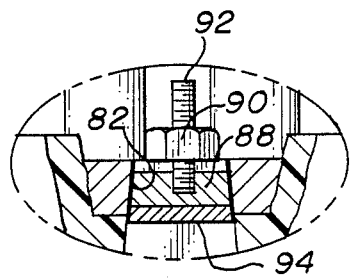
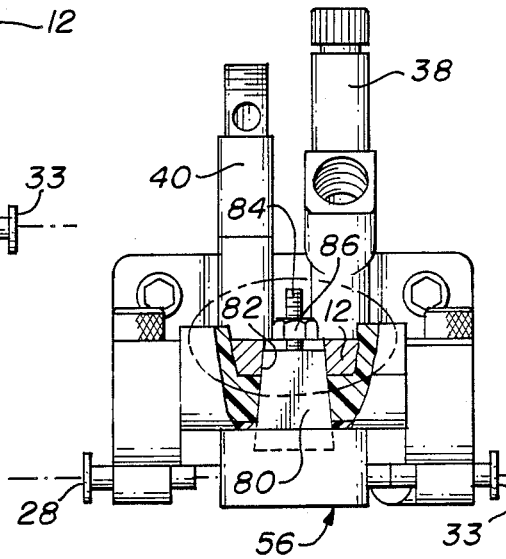

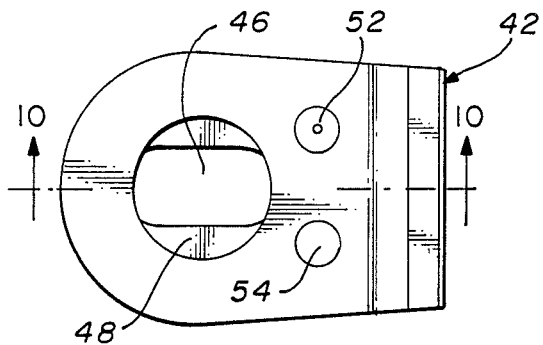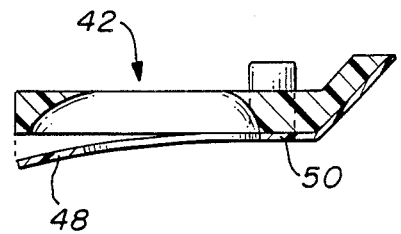
FIG. 9  FIG. 10
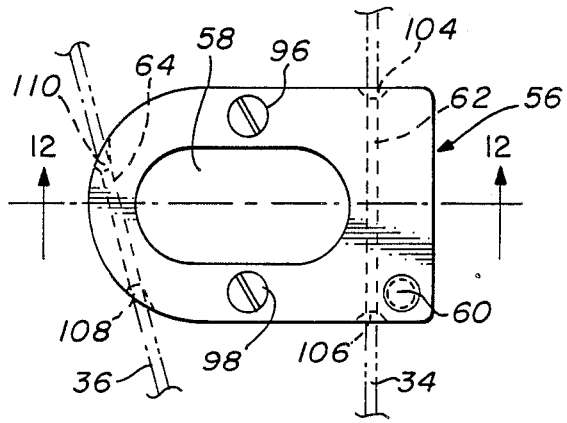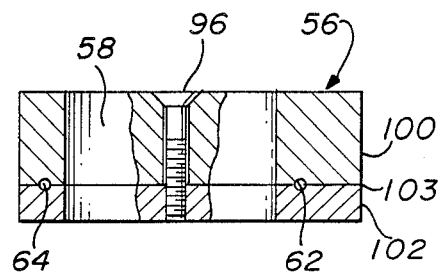
FIG. 11  FIG. 12
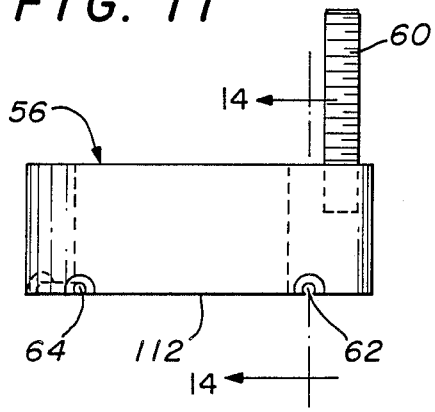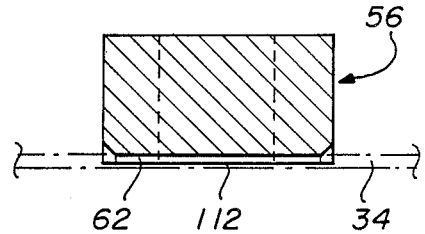
FIG. 13  FIG. 14

DRILL BIT GUIDE

BACKGROUND OF THE INVENTION

The present invention relates to a method and apparatus for use in cementing a femoral stem hip prosthesis in the medullary canal of a resected femur and in particular relates to an improved drill bit guide which enables a prosthesis fixture to be attached to the femoral cortex of the resected femur with the use of drill bits or fixation pins passing through the fixture and through the femoral cortex more quickly and accurately than has been done previously.

In U.S. Pat. No. 4,357,716, issued Nov. 9, 1982, there is disclosed a method and apparatus for mounting a femoral stem hip prosthesis in a femoral canal with the use of a cement. Disclosed therein is a prosthesis fixture which mounts the femoral stem of the prosthesis in the femoral canal in a rigid relationship thereto so that the prosthesis stem can be cemented in the canal under pressure while in the rigid relationship to provide a strong bond between the prosthesis stem and the femur. The prosthesis fixture includes a base guide which is generally U-shaped and which has opposing orifices in the legs of the U-shaped guide which are in alignment with each other. These orifices are utilized for a fixation pin or drill bit (hereinafter called "pin") which is driven through the cortex of the femur in order to hold the base guide in a rigid relationship thereto.

These orifices are made only slightly larger than the pins which are used and it has been found that if there is any slight migration of the pin as it passes through the femoral cortex it may not precisely line up with the orifice on the opposite side of the U-shaped guide. This causes the pin to strike the guide itself instead of the orifices thereby requiring the pin to be reset. This not only requires the pin to be re-aligned but of course also increases the required time for the surgery.

In commonly owned co-pending application Ser. No. 734,559, filed May 16, 1986 and entitled IMPROVED DEVICE AND METHOD FOR CEMENTING A HIP PROSTHESIS IN A FEMORAL CANAL, an improvement in the method and apparatus for driving the pins through the base guide was disclosed. A first orifice was provided in one side of the guide for inserting a pin and a second orifice was was inserted in another side of the guide which is much larger in cross-section than the pin. An easily penetrable material such as a cylindrical plastic plug was inserted in the second orifice wherein the pin, in passing through the first orifice and the femoral cortex, could deviate from axial alignment and still strike the plastic plug in the receiving orifice and pass therethrough. Thus the metal frame of the base guide is not touched and yet the pin may deviate somewhat from axial alignment and still penetrate the plastic plug. The plastic plug is threaded and so is the second receiving orifice in which it is inserted so that after the base guide has been used in one operation, the plastic plug can be threadably removed and a new one threadably inserted so that the guide can be used again in the next operation.

Obviously, these prior art methods require excessive amounts of time to insert the Kirschner wires or pins or drill bits if the pins or bits tend to migrate when they reach the cortical bone surface. Of course where the plastic plug is used, the plug must be removed and replaced as needed. Further, if for any reason it is required that the pins or the drill bits be removed and then replaced, the orifices which were formed with a migrating drill bit may not be aligned and thus it may not be possible to re-insert the pins or bits without drilling new orifices.

To overcome the disadvantages of the prior art, applicant provides bit guides which enable the surgeon to drill the orifices more quickly and more accurately than can be accomplished with the prior art methods and apparatus. The improved guide establishes a drill bit path through one leg of the U-shaped base guide, the femoral cortex and the other leg of the U-shaped guide. Thus, a drill bit sleeve is mounted in each orifice in the legs of the U-shaped base guide for guiding the drill bit inserted in the sleeve through the cortex of the femur. The bit sleeves comprise a hollow tube snugly but movably mounted in each of the orifices in the legs of the U-shaped base guide for movement toward and away from the femoral cortex. This enables the sleeve to be moved inwardly and pressed against the femoral cortex thus guiding the drill bit and holding it firmly at the surface of the bone where migration of the bit could occur. Thus migration of the bit is prevented by the bit sleeve and is caused to pass through the cortical bone in a straight line. A shoulder is formed on the outer end of the hollow tube for limiting inward movement of the sleeve toward the cortex and a countersunk opening is formed in each end of the hollow tube for guiding a received drill bit into the hollow bit sleeve.

In addition, once the drill bit has passed through the cortical bone into the medullary canal, it again encounters cortical bone on the opposite side of the medullary canal and again, the drill bit may have a tendency to migrate. Thus the present invention provides for an annular body member for receiving the prosthesis stem and forming a drill bit guide for insertion in the medullary canal. The annular body is rigidly attached to the fixture holding the prosthesis. Passageways extend through the medullary body member in alignment with the opposed orifices in the legs of the U-shaped base guide and thus each receives a drill bit as it passes from the bit sleeve in an orifice in the leg of the U-shaped base guide. The annular body member may be a one piece member having a continuous wall and has a shape comparable to the shape of the periphery of the medullary canal. Thus the passageways provide a guide for the drill bit as it attempts to penetrate the cortical bone on the other side of the medullary canal. Each of the passageways in the annular body member have a countersunk opening at each end thereof for guiding a received drill bit into the passageway.

Thus it is an object of the present invention to provide bit sleeves in the orifices of the base guide to keep the drill bit in a fixed, predetermined path through the cortical bone of the femur and prevent deviation of the bit from a straight path.

It is also an object of the present invention to use a bit sleeve in the orifices of the prosthesis fixture which are snugly but movably mounted in each of the orifices for movement toward and away from the femoral cortex such that they can be moved against the cortical bone to prevent migration of the drill bit as it attempts to penetrate the cortical bone.

It is also an object of the present invention to provide an annular body member as a drill bit guide which is inserted in the medullary canal to establish a drill bit travel path through the medullary canal from the cortical bone on one side of the canal to the cortical bone on the other side of the canal.

It is yet another object of the present invention to provide an annular body member as a bit guide for insertion in the medullary canal between the two cortises of bone.

It is still another object of the present invention to provide an annular body as a drill bit guide having passageways extending through the body member in alignment with opposed orifices in the legs of the U-shaped base guide for receiving and guiding the drill bits through the cortical bone.

SUMMARY OF THE INVENTION

Thus the present invention relates to an improved drill bit guide for use in cementing a femoral stem hip prosthesis in the medullary canal of a resected femur, said guide including a U-shaped base guide adapted to be rigidly attached to the proximal end of said resected femur with fixation pins or drill bits passing through opposed orifices in the legs of said U-shaped base guide and the cortex of said femur and a ceiling fixture rigidly attached to said base guide for holding said femoral prosthesis in a fixed position in said medullary canal, the improved guide establishing a drill bit travel path through one leg of the U-shaped base guide, the femoral cortex and the other leg of said U-shaped base guide, the improved guide comprising an annular body member for receiving said prosthesis stem and forming a drill bit guide for insertion in said medullary canal, means for rigidly attaching said annular body member to said ceiling fixture, and at least one passageway extending through said medullary body member in alignment with said opposed orifices in said legs of said U-shaped base guide for receiving said drill bit and guiding said bit through a predetermined path in said cortex.

The invention also relates to an improvement in apparatus for attaching a prosthesis fixture to the femoral cortex on a resected femur with the use of drill bits or fixation pins passing through orifices in said fixture and through said femoral cortex, the improvement comprising an annular body member forming a drill bit guide for insertion in the medullary canal of the resected femur, means for rigidly attaching said annular body member to said ceiling fixture, and passageways extending through said medullary body member in alignment with said opposed orifices in said fixture for receiving and guiding drill bits passing through said fixture and said femoral cortex.

The invention also relates to a method of guiding drill bits or pins during the process of cementing a femoral stem hip prosthesis in the medullary canal of a resected femur, said process including the steps of rigidly attaching a U-shaped base guide to the proximal end of said resected femur with fixation pins or drill bits passing through opposed orifices in the legs of said U-shaped guide and the cortex of said femur and rigidly attaching a ceiling fixture to said base guide for holding said femoral prosthesis in a fixed position in said medullary canal, said method comprising the steps of extending passageways through the wall portions of an annular body member, inserting said annular body member in said medullary canal for receiving said prosthesis stem, aligning said passageways in said annular body member with said opposed orifices in said legs of said U-shaped base guide for receiving and guiding said drill bits through said femoral cortex, and rigidly attaching said annular body member to said ceiling fixture to form a drill bit guide for directing said drill bit travel path through said femoral cortex.

BRIEF DESCRIPTION OF THE DRAWINGS

These and other objects of the present invention will be disclosed more fully in conjunction with the accompanying drawings in which like numbers represent like components and in which:

FIG. 1 is an isometric representation of the assembled prosthesis fixture for attachment to the femur for cementing the prosthesis in the femoral canal and including the U-shaped base guide having the drill bit guide sleeves mounted therein;

FIG. 2 is an exploded isometric view of the fixture in FIG. 1 illustrating the various components thereof and, in particular, illustrating the base guide with its drill bit guide sleeves and the medullary bit guide;

FIG. 3 is an isometric view of the U-shaped bit base guide with the bit sleeves therein and the medullary canal bit guide being shown with the drill bits or pins passing through the drill bit sleeves in the U-shaped base guide and the passageways in the medullary canal bit guide;

FIG. 4 is a plan view of the base guide, the femoral cortex, the bit guide in the medullary canal and the drill bit sleeves in the orifices of the base guide illustrating how the pins or drill bits pass through the bit sleeves in the legs of the base guide, through the cortical bone of the femur, through the passageways in the medullary canal bit guide, through the other side of the femoral cortex and finally through the bit sleeve in the opposing orifice in the opposing leg of the base guide;

FIG. 5 is a cross-sectional view taken along a longitudinal axis of a drill bit sleeve illustrating the construction thereof;

FIG. 6 is a rear view of a partially cut-away fixture illustrating one manner in which the medullary canal bit guide is rigidly attached to the ceiling;

FIG. 7 is a rear view of a fixture having a partial cross-section to illustrate an alternative manner of rigidly attaching the medullary canal bit guide to the ceiling;

FIG. 7A is an enlarged view of a portion of FIG. 7 to more clearly illustrate the details of the wedge-shaped body used to seal the opening in the ceiling fixture after the medullary canal bit guide is removed;

FIG. 8 is a top view of the device shown in FIG. 7 and FIG. 7A to illustrate the manner in which the medullary canal bit guide or the wedge-shaped body can be rigidly attached to the ceiling;

FIG. 9 is a plan view of the silicone sealer;

FIG. 10 is a cross-sectional view of the silicone sealer shown in FIG. 9;

FIG. 11 is a plan view of a second embodiment of the medullary canal bit guide;

FIG. 12 is a cross-sectional view of the bit guide of FIG. 11;

FIG. 13 is a side view of a second embodiment of a medullary canal bit guide; and FIG. 14 is a cross-sectional view of the bit guide of FIG. 13.

DETAILED DESCRIPTION OF THE DRAWINGS

As pointed out in U.S. Pat. No. 4,357,716, which patent is incorporated herein in its entirety by reference, a prosthesis fixture is necessary to hold the stem of a prosthesis in a fixed relationship in the prepared femoral canal while a determination can be made of the proper position of the prosthesis stem within the canal and to enable the cement to be applied to the femoral canal under pressure with the pressure being maintained while the cement is drying. Such a fixture 10 is illustrated in its assembled form in FIG. 1. The fixture comprises a ceiling 11 comprised of a first half 12 and a second half 14 which are connected by appropriate bolts or other fastening devices 16. The ceiling halves 12 and 14 are rigidly attached to a base guide 18 by fastener means such as bolts or screws 20. As will be seen in FIG. 2, base guide 18 is generally U-shaped and has orifices such as those shown at 22, 23, 24 and 26 in which drill bit sleeves 28, 30, 32 and 33 are inserted. Drill bits or Kirschner pins 34 and 36 are illustrated by dashed lines as extending through opposed orifices on opposing sides or legs of the U-shaped base guide 18. Attachments 38 and 40 on ceiling 11 are inlet and outlet valves for the insertion of cement into the femoral canal under pressure to rigidly attach a femoral prosthesis in the femoral canal as explained in U.S. Pat. No. 4,357,716.

FIG. 2 is an exploded view of the fixture 10 shown in FIG. 1. As can be seen in FIG. 2, the ceiling 11 is constructed in two halves 12 and 14 along line 44 to enable the unit be easily placed around and over the neck and/or collar of the prosthesis. Fixtures 38 and 40 are inlet and outlet valves which are threadably attached to appropriate orifices in ceiling halve 12 and enable cement to be injected into a femoral canal under pressure when the unit is attached to the resected femur. Bolts 20 or other attaching means are used to rigidly attach the ceiling to the base guide 8.

A silicone sealer 42 is used to prevent the cement from reaching the ceiling halves 12 and 14 so that the cement will not be able to adhere to the ceiling halves 12 and 14. As explained in U.S. Pat. No. 4,357,716 the sealer 42 may be made of two pieces instead of one as shown in FIG. 2 herein. Sealer 42 consists of a plastic, approximately ⅛ inch thick, usually a rubbery material such as commercially available polyform or isoprene or it may be made of silicone material such as Silastic (Dow-Corning) and the use of the word "plastic" herein in relation to said sealer 42 is inclusive of any of these materials. The prosthesis stem, extending from the ceiling halves 12 and 14 is inserted through the orifice 46 in silicone sealer 42. A lower lip 48 is formed with silicone sealer 42 and is attached only at the rear portion 50. This lip or flap 48 is valuable when the prosthesis being used has a collar. Some of them do not. Where there is a collar on the prosthesis, the flap 48 is located under the collar while the sealer 42 itself is above the collar thus protecting it from cement adhesion. Orifices 52 and 54 are provided for the insertion of the cement into the femoral canal.

The medullary bit guide 56 is an annular body member formed as a continuous wall which has a central opening 58 through which the prosthesis stem is inserted. The entire medullary bit guide 56 is sized for insertion in the medullary canal as will be shown hereafter in relation to FIG. 4. This means, of course, that different sizes would be available for different sizes of the medullary canals. It has a fastening device such as a bolt 60 which can be used to rigidly attach the annular body member 56 to the ceiling fixture halve 12. Passageway 62 and 64 extend through the medullary body member for alignment with corresponding opposed orifices in base guide 18. Thus when the fixture is assembled as shown in FIG. 1, the passageway 62 in the medullary bit guide 56 will be in alignment with orifices 22 and 23 in the legs of the U-shaped base guide 18 while passageway 64 will be in alignment with opposed orifices 24 and 26 in base guide 18. Bit sleeves 28, 30, 32 and 33 are inserted in orifices 22, 24, 26 and 23 respectively.

As stated earlier, the apparatus to be secured to the bone requires that pins or drill bits be inserted through the orifices in the base guide and through the cortical bone. The surgeon has a choice of using malleable drill bits or Kirschner pins which tend to bend or stiff bits which may break. Either type of drill bit or pin tends to migrate when attempting to penetrate the bone. This is especially true when the bit or pin makes contact with the bone surface which is not perpendicular to the longitudinal axis of the drill bit. To overcome this problem, the novel drill bit guide shown in FIG. 4 has been developed. The addition of bit sleeves 28, 30, 32 and 33 in the base guide 18 and the bit guide 56 in the medullary canal 66 which lies between the cortises of bone 68 and 70 will enable the surgeon to drill the holes through the cortical bone of the resected femur more quickly and more accurately than was previously possible. Bit sleeves 28, 30, 32 and 33 fit snugly but movably in each of the orifices 22, 24, 26 and 23. This enables the bit sleeves to move toward and away from the cortical bone walls 68 and 70. Thus it can be seen that without sleeve 28 in FIG. 4, if drill bit 34 is inserted in orifice 22, as the bit 34 approaches cortical bone wall 68, there is a space 72 through which it must pass which enables the bit to migrate as it attempts to penetrate cortical bone wall 68. By using sleeve 28, and pushing sleeve 28 so that it rests against cortical bone 68 as shown in FIG. 4, the drill bit is prevented from migrating and is caused to quickly penetrate and pass directly through cortical bone 68 where it encounters passageway 62 in the medullary canal bit guide 56. Because the bit guide 56 is inserted in the medullary canal, the sides thereof are necessarily in close proximity to the cortical bone walls 68 and 70. Although gaps are shown in FIG. 4, for purposes of illustration, in actual practice the bit guide 56 is very close to the cortical bone wall structures 68 and 70. Thus as drill bit 34 exits from passageway 62 it is essentially abutting the cortical bone wall 70 and again is prevented from migrating because of passageway 62. Again, the bit easily penetrates cortical bone 70 and passes directly through and into bit sleeve 33. The pin or drill bit 36 functions in a similar manner with respect to bit sleeves 30 and 32 and passageway 64 in bit guide 56.

FIG. 5 is a cross-sectional view of one of the bit sleeves 28. It will be noted first that a collar 74 is formed on one end thereof to limit the movement of bit sleeve 28 toward the base guide 18. The space 72 between the base guide 18 and the cortical bone wall structures 68 and 70 varies with the size of the individual femur to which the base guide 18 is being attached. Thus there will be more or less of bit sleeve 28 protruding from base guide 18 depending upon that space 72. As shown in FIG. 5, each end of sleeve 28 has an opening which is countersunk. Thus one end is counter sunk at 76 and the other end is countersunk at 78. This allows for easy insertion of the drill bit or pin into the sleeve 28. In like manner, end 78 allows easy insertion of the pin or drill bit as it emerges from the cortical bone wall structure 70 and aligns itself with the bit sleeve (such as sleeve 33) in the opposing orifice in the opposite leg of base guide 18.

FIG. 6 is a partial cross-sectional view of the rear of the fixture 10 shown in FIG. 1. It illustrates the manner in which the medullary canal bit guide 56 is rigidly attached to the ceiling 12. As can be seen in FIG. 6, the threadable means 60, which may be a bolt, extends through orifice 61 of the half 12 of the ceiling 11 where it is engaged by threads on fixture 40. By tightening fixture 40 about the threads of bolt 60, the medullary canal bit guide 56 is held rigidly against the silicone sealer 42. There is some resiliency in the silicone sealer 42 but essentially the bit guide 56 is held in a rigid relationship with respect to the one-half 12 of the ceiling 11.

FIG. 7 is a partial cross-sectional rear view of the fixture illustrated in FIG. 1, illustrating an alternative structure for rigidly attaching the bit guide 56 to the one-half 12 of the ceiling 11. As can be seen in FIG. 7, a wedge-shaped body 80 is rigidly attached to the medullary canal bit guide 56 in any well-known manner and fits into a corresponding wedge shaped slot 82 in one-half 12 of the ceiling 11. A threaded post or bolt 84 is rigidly attached to the wedge-shaped body portion 80 and with the use of a nut 86 the wedge-shaped portion 88 is pulled snugly into the wedge-shaped slot 82 of the one-half 12 of the ceiling 11 thus securely fastening the medullary canal bit guide 56 to the one-half 12 of the ceiling 11. Prior to the introduction of cement into the medullary canal, the medullary canal guide 56 will have to be removed from slot 82 in ceiling 11 and consequently a plug 88 will have to be fit into the slot 82 to prevent cement from exiting through the slot. This can be done by utilizing a wedge-shaped body 88 having a bolt 92 to which nut 90 is threadably attached. Thus the wedge 88 can be drawn tightly into the slot 82 and the slot is closed with wedge 88. The lower portion 94 of wedge 88 should be made of silicone or elastomer or some other material 94 which would not adhere to the cement which is used to cement the prosthesis in the femoral canal.

FIG. 8 is a top view of the rear portion of the fixture 10 shown in FIG. 7 to illustrate the slot 82 in which wedge shaped body 80 or 88 is inserted.

FIG. 9 is a plan view of the silicone sealer 42 illustrating the orifices 52 and 54, the orifice 46 through which the prosthesis stem is inserted and the lower lip 48.

FIG. 10 is a cross-sectional view of the silicone sealer 42 illustrating the attachment of the lower lip 48 at the rear portion 50.

FIG. 11 and FIG. 12 are plan views and cross-sectional views respectively of an alternative form of the medullary bit guide 56. As can be seen in both of those figures, the bit guide 56 is an annular body member formed of a continuous wall member which has a central opening 58 through which the prosthesis stem is inserted. Passageways 62 and 64 extend through the bit guide 56 as stated previously for alignment with corresponding opposed orifices in base guide 18 as shown in FIG. 4. In the embodiment shown in FIG. 2 and FIG. 4, it is necessary, once the pins 34 and 36 have been inserted through the cortical bone 68 and 70 of the femur, to remove the pins and the entire fixture 10 so that the medullary bit guide can be removed. The device is then reassembled with the prosthesis as a part of it and is re-attached to the femur by inserting the pins 34 and 36 in the previously drilled holes in the cortical bone. The embodiment shown in FIG. 11 and FIG. 12 avoids the necessity for removing the base guide 18 and the pins 34 and 36. With the embodiment shown in FIG. 11 and FIG. 12, it is only necessary to remove the ceiling 11 by removing bolts 20 and then remove the prosthesis. At that point, screws 96 and 98 are removed and, as can be seen in FIG. 12 because the bit guide 46 is formed in two mating pieces 100 and 102 separated by a common plane 103 passing through the longitudinal axis of the passageways 62 and 64. Thus one-half of each passageway is formed in each mating portion 100 and 102. With the pins 34 and 36 passing through orifices 62 and 64, the upper portion 100 and the lower portion 102 can be separately removed from about the pins 34 and 36 thus allowing the bit guide 56 to be removed in two pieces without the necessity of removing the pins 34 and 36 an/or the base guide 18. It will be noted that each of the passageways 62 and 64 has a countersunk opening at each end thereof at locations 104, 106, 108 and 110 for guiding a received pin or drill bit into the respective passageways 62 and 64.

The embodiment shown in FIG. 13 and 14 is another embodiment which is useful in enabling the bit guide 56 to be removed without removing either the pins 34 and 36 from the cortical bone walls 68 and 70 or without removing base guide 18. In this case it will be noted that the passageways 62 and 64 are formed in and parallel to the bottom surface 112 of a portion of the continuous wall of the bit guide 56 with each of the orifices 62 and 64 having an arcuate cross-section greater than 180° but less than 360° so as to expose a sufficient portion of a drill bit 34 inserted therein to enable the one piece bit guide 56 to be removed from drill bit 34 and 36 without removing the drill bits from the femoral cortex. In other words, the passageways are formed so as to guide and hold the drill bits 34 and 36 but can be removed therefrom through the exposed portion of the passageways.

Thus there has been disclosed an improved drill bit guide which enables a prosthesis fixture to be attached to the femoral cortex of a resected femur with the use of drill bits or fixation pins passing through the fixture and the femoral cortex more quickly and accurately than has been done previously. The use of bit sleeves in the base guide which are movable toward and away from the cortical bone hold the drill bit or fixation pin firmly against the cortical bone to prevent migration thereof during the process of driving the bit or pin through the bone. In addition, the medullary canal bit guide having passageways therein aligned with the orifices in the base guide receive the drill bit or fixation pin as it passes into the medullary canal and guides it to the other side of the canal to the cortical bone and again holds the pin or drill bit firmly against the bone and prevent migration thereof as the pin is driven through the bone where it is received by the bit sleeve passing through the base guide on the other side of the femur. This allows such cortical bone orifices to be drilled accurately and more quickly than has been done previously.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim:

1. An improved drill bit guide for use in cementing a femoral stem hip prosthesis in the medullary canal of a resected femur, said bit guide including a U-shaped base guide adapted to be rigidly attached to the proximal end of said resected femur with fixation pins or drill bits passing through opposed orifices in the legs of said U-shaped base guide and the cortex of said femur and a ceiling fixture rigidly attached to said base guide for holding said femoral prosthesis in a fixed position in said medullary canal, said improved guide establishing a drill bit travel path through one leg of said U-shaped base guide, said femoral cortex and the other leg of said U-shaped base guide, said improved guide comprising:

a. an annular body member having the general shape of the medullary canal for receiving said prosthesis stem and forming a drill bit guide for insertion in said medullary canal, b. means for rigidly attaching said annular body member to said ceiling fixture, and c. at least one passageway extending through said annular body member in alignment with said opposed orifices in said legs of said U-shaped base guide for receiving said drill bit and guiding said bit in a predetermined path through said cortex of said femur.

2. An improved guide as in claim 1 further including a drill bit sleeve mounted in each orifice in the legs of said U-shaped base guide for guiding said drill bit inserted in said sleeve through said cortex of said femur and said aligned passageways in said annular body member so as to enable the drill bits to pass through said femoral cortex more quickly and accurately.

3. An improved guide as in claim 2 wherein said bit sleeve comprises:

a. a hollow tube snugly but movably mounted in each of said orifices in the legs of said U-shaped base guide for movement toward and away from said femoral cortex, b. a shoulder on the outer end of said hollow tube for limiting inward movement of said sleeve toward said cortex, and c. a countersunk opening in each end of said hollow tube for guiding a received drill bit into said hollow tube.

4. An improved guide as in claim 1 wherein said rigid attaching means for said annular body member comprises:

a. a threaded member fixedly attached to said body member and extending toward said ceiling fixture, b. an orifice in said ceiling for receiving said threaded member, and c. fastening means for mounting on said threaded member to rigidly secure said body member to said ceiling fixture.

5. An improved guide as in claim 4 wherein:

a. said threaded member comprises a wedge-shaped body having a threaded bolt integrally formed therewith, and b. said orifice in said ceiling is wedge-shaped to receive said threaded member.

6. An improved guide as in claim 1 wherein said medullary canal annular body member comprises:

a. first and second mating portions separated by a common plane passing through the longitudinal axis of all passageways formed in said body member so as to create one-half of each passageway in each mting portion and b. means for removably attaching said mating portions to each other to form said passageways so that said mating portions can be removed from said medullary canal without removing said drill bits passing through said legs of said U-shaped guide and said femoral cortex.

7. An improved guide as in claim 1 wherein said medullary canal annular body member comprises:

a. a one piece member having a continuous wall forming said annular body and b. said passageways being formed in and parallel to the bottom surface of a portion of said continuous wall and each having an arcuate cross-section greater than 180° but less than 360° so as to expose a portion of said drill bit inserted therein to enable said one piece member to be removed from a drill bit without removing said drill bit from said femoral cortex.

8. An improved drill bit guide as in claim 1 wherein each of said passageways in said body member has a countersunk opening at each end thereof for guiding a received drill bit into said passageway.

9. In an apparatus for attaching a prosthesis fixture to the femoral cortex of a resected femur with the use of drill bits or fixation pins passing through opposed orifices in said fixture and through said femoral cortex, the improvement comprising:

a. an annular body member forming a drill bit guide for insertion in the medullary canal of said resected femur, b. means for rigidly attaching said annular body member to said fixture, and c. at least one passageway extending through said annular body member in alignment with said opposed orifices in said fixture for receiving and guiding a drill bit passing through said fixture and said femoral cortex.

10. The improvement of claim 9 wherein each of said passageways in said body member has a countersunk opening at each end thereof for guiding a received drill bit into said passageway.

11. The improvement of claim 9 wherein said body member is annular in shape to receive said prosthesis and to conform to the shape of said medullary canal for insertion therein.

12. A method of guiding drill bits or pins during the process of cementing a femoral stem hip prosthesis in the medullary canal of a resected femur, said process including the steps of rigidly attaching a U-shaped base guide to the proximal end of said resected femur with fixation pins or drill bits passing through opposed orifices in the legs of said U-shaped base guide and the cortex of said femur and rigidly attaching a ceiling fixture to said base guide for holding said femoral prosthesis in a fixed position in said medullary canal, said method comprising the steps of:

a. extending at least one passageway through wall portions of an annular body member, b. inserting said annular body member in said medullary canal for receiving said prosthesis stem, c. aligning said at least one passageway in said annular body member with said opposed orifices in said legs of said U-shaped base guide for receiving and guiding said drill bits through said femoral cortex, and d. rigidly attaching said annular body member to said ceiling fixture to form a drill bit guide for directing said drill bit travel path through at least a portion of said femoral cortex.

13. A method as in claim 12 further including the step of mounting a drill bit sleeve in each orifice in each leg of said U-shaped base guide for guiding said drill bit inserted in said sleeve into said femoral cortex and said aligned passageways in said annular body member so as to enable said drill bit to pass through said femoral cortex in a straight line more quickly and accurately.

14. A method as in claim 13 wherein the step of mounting said drill bit sleeve comprises the steps of:
   a. mounting a hollow tube snugly but movably in each of said orifices in the legs of said U-shaped base guide for movement toward and away from said femoral cortex to guide said drill bit to the surface of said cortex,
   b. limiting inward movement of said sleeve toward said cortex by means of a shoulder formed on the outer end of said hollow tube, and
   c. countersinking an opening in each end of said hollow tube for guiding a received drill bit into said hollow tube.

15. A method as in claim 12 wherein the step of rigidly attaching said annular body member to said ceiling fixture comprises the steps of:
   a. fixedly attaching a threaded fixture to said annular body member,
   b. extending said threaded fixture to said ceiling fixture,
   c. receiving said threaded fixture through an orifice in said ceiling, and
   d. mounting a fastening device on said threaded fixture to rigidly secure said annular body member to said ceiling fixture.

16. A method as in claim 15 further comprising the steps of:
   a. forming said threaded fixture as a wedge-shaped body having a threaded bolt integrally formed therewith, and
   b. forming said orifice in said ceiling fixture in a corresponding wedge shape for receiving said threaded bolt to be secured with said fastening device.

17. A method as in claim 12 further comprising the steps of:
   a. forming said annular body member of first and second mating portions separated by a common plane passing through the longitudinal axis of all passageways formed in said wall portion of said annular body member so as to create one-half of each passageway in each mating portion, and
   b. removably attaching said mating portions to each other to form said passageways so that said mating portions can be removed from said medullary canal without removing said drill bits passing through said legs of said U-shaped guide and said femoral cortex.

18. A method as in claim 12 further including the steps of:
   a. forming said annular body of a one-piece member having a continuous wall, and
   b. forming said passageways in and parallel to the bottom surface of said wall, such that each passageway has an arcuate cross-section greater than 180° but less than 360° so as to expose a portion of said drill bit inserted therein and enable said one piece body member to be removed from a drill bit without removing said drill bit from said femoral cortex.

19. A method as in claim 12 further comprising the step of countersinking an opening at each end of said passageways in said body member for guiding a received drill bit into said passageway.

20. A method for attaching a prosthesis fixture to the femoral cortex of a resected femur with the use of drill bits or fixation pins passing through opposed orifices in said fixture and through said femoral cortex, the improvement comprising the steps of:
   a. forming an annular body member as a drill bit guide for insertion in the medullary canal of said resected femur,
   b. extending at least one passageway through said annular body member,
   c. aligning said at least one passageway in said body member with said opposed orifices in said fixture for receiving and guiding drill bits passing through said fixture and said femoral cortex, and
   d. rigidly attaching said annular body member to said prosthesis fixture.

21. A method as in claim 20 further including the step of countersinking openings at each end of said body member passageways for guiding a received drill bit into said passageway.

* * * * *

UNITED STATES PATENT AND TRADEMARK OFFICE
CERTIFICATE OF CORRECTION

PATENT NO. : 4,834,080

DATED : May 30, 1989

INVENTOR(S) : Byron L. Brown

It is certified that error appears in the above-identified patent and that said Letters Patent is hereby corrected as shown below:

Column 9, line 62, "mting" should read -- mating --.

Signed and Sealed this

Thirteenth Day of March, 1990

*Attest:*

JEFFREY M. SAMUELS

*Attesting Officer*   *Acting Commissioner of Patents and Trademarks*